(12) United States Patent
Wahl et al.

(10) Patent No.: US 6,936,149 B2
(45) Date of Patent: Aug. 30, 2005

(54) GAS SENSOR

(75) Inventors: Thomas Wahl, Pforzheim (DE); Torsten Handler, Stuttgart (DE); Harry Braun, Heimsheim (DE); Sven Boeffert, Straubenhardt-Offenhausen (DE); Lothar Diehl, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 368 days.

(21) Appl. No.: 10/114,000

(22) Filed: Apr. 1, 2002

(65) Prior Publication Data

US 2002/0175077 A1 Nov. 28, 2002

(30) Foreign Application Priority Data

Mar. 30, 2001 (DE) .......................................... 101 15 872

(51) Int. Cl.[7] .............................................. G01N 27/41
(52) U.S. Cl. ....................... 204/427; 204/426; 73/23.32
(58) Field of Search ................................ 204/424, 425, 204/426, 427, 428, 429; 73/23.31, 23.32, 23.22

(56) References Cited

U.S. PATENT DOCUMENTS

| | | | | |
|---|---|---|---|---|
| 4,824,548 A | * | 4/1989 | Iino et al. ................... 204/406 |
| 4,882,033 A | * | 11/1989 | Shibata et al. ............... 204/425 |
| 4,900,425 A | * | 2/1990 | Sasayama et al. ........... 204/426 |
| 4,909,922 A | * | 3/1990 | Kato et al. ................... 204/406 |
| 5,672,811 A | * | 9/1997 | Kato et al. ................. 73/31.05 |
| 6,036,841 A | * | 3/2000 | Kato et al. ................... 205/781 |
| 6,096,187 A | * | 8/2000 | Mizoguchi et al. ...... 205/784.5 |

FOREIGN PATENT DOCUMENTS

DE 198 15 700 10/1999

* cited by examiner

Primary Examiner—Kaj K. Olsen
(74) Attorney, Agent, or Firm—Kenyon & Kenyon

(57) ABSTRACT

A gas sensor for determining a physical quantity of a gas component, e.g., in an exhaust gas of an internal combustion engine, including a sensor element which contains at least one electrochemical cell. The electrochemical cell includes a first electrode and a second electrode that are arranged at a distance on at least one solid electrolyte, the second electrode is arranged in a reference gas space. A third electrode which is in contact with a gas located in the gas space is provided. The gas component may be exchanged between the gas space and the reference gas space using a voltage applied between the second electrode and the third electrode.

17 Claims, 3 Drawing Sheets

GAS SENSOR

FIELD OF THE INVENTION

The present invention relates to a gas sensor.

BACKGROUND INFORMATION

Gas sensors of similar kind are described for example in German Published Patent Application No. 198 15 700. Such a gas sensor has a potentiometrically driven electrochemical cell including a first and a second electrode and a solid electrolyte arranged between the first and second electrodes. The first electrode is coated with a porous protective film and is in contact with a measuring gas located outside the sensor element. The second electrode is arranged in a reference gas space, which is at least partly filled with a porous material. A heater is be provided for the purpose of heating the sensor element in a measurement area, and is separated from the solid electrolyte coatings that surround it by a heater insulation.

If differing oxygen partial pressures arise in the measuring gas outside the sensor element and the reference gas in the reference gas space, a Nernst voltage is formed between the first and the second electrode, which may be calculated using electronic evaluation means located outside the sensor element. The Nernst voltage may be used to determine the ratio of the oxygen partial pressures in the measuring gas and the reference gas.

Moreover, the electronic evaluation means creates an electrical pumping voltage between the first and the second electrode, which causes oxygen to be pumped into the reference gas space via the first and the second electrodes. As a consequence, there is always adequate oxygen partial pressure in the reference gas space, regardless of the operating conditions. An alternating voltage is also applied between the first and the second electrodes to regulate the heater. The electronic evaluation arrangement may be used to calculate the temperature of the sensor element's measurement area from the temperature-dependent impedance, so that the heater may be switched on or off.

The disadvantage of the conventional gas sensor is that the generation of a voltage serving to pump the reference gas space at the potentiometrically driven electrochemical cell causes the probe signal to be distorted by polarization effects, particularly at the first electrode. The polarization effects are stronger at low probe temperatures, which are present particularly in the case of a gas sensor arranged on the gas outlet side of a catalytic converter.

SUMMARY

The gas sensor according to the present invention may provide that pumping into and out of the reference gas space may be effected by applying a voltage between a second electrode, arranged in the reference gas space, and a third electrode. In this manner, the function of an electrochemical cell that may be formed by a first and the second electrodes and by a solid electrolyte arranged between the first and the second electrodes may not be disrupted. For this purpose, the third electrode may be arranged on a solid electrolyte and may be in contact with an area containing a gas.

If a pumping voltage exists between the second and third electrodes such that oxygen is regularly pumped into the reference gas space, which may be filled with a porous material, the level of the oxygen partial pressure in the reference gas space may always be adequate, regardless of operating conditions. Thus the measurement result of the gas sensor obtained with the Nernst voltage may not be distorted by a drop in the oxygen partial pressure in the reference gas space. Contaminants may also be prevented from infiltrating the reference gas space.

If an alternating voltage is applied between the second and third electrodes to determine the temperature in the measurement area of the sensor element, the measuring function of the electrochemical cell is influenced only minimally, if at all, by the alternating voltage. Moreover, a larger internal resistance may be provided between the second and the third electrode, and/or between the first and the third electrode, for example, by the fact that the third electrode has a smaller surface area than the second and/or first electrode. As a result, the impedance may be calculated more easily using, for example, an analog-to-digital converter contained in the electronic evaluation arrangement.

The measurement area of the sensor element may be heated with a heater which may include a first and a second heater lead in the supply area. The heater leads may be electrically connected by feedthroughs to contact surfaces on an exterior surface of the sensor element. The first heater lead may be set to a constant potential, the potential of the second heater lead may be varied by the electronic evaluation arrangement. In an example embodiment of the present invention, the third electrode may be electrically connected to the first heater lead, so that no power supply wire may be needed for the third electrode.

In an example embodiment of the present invention, the third electrode may be arranged on an external surface of the sensor element and may be covered with a gas-permeable protective film.

A simple construction of the sensor element may be achieved if the sensor element includes a heater having heater insulation that is porous and is in contact with a gas outside the sensor element, and if the third electrode is attached between the heater insulation and an adjacent solid electrolyte, and is in contact with the gas located in the porous heater insulation.

The construction may be further simplified if the heater has a porous heater insulation and if the first heater lead is arranged at least in part between the heater insulation and one of the adjacent solid electrolytes, so that the first heater lead may be used at least in part as the third electrode. Since the first heater lead may have a constant potential, there may be no danger of capacitive coupling between the heater and an electrochemical cell, and therefore the first heater lead may not need to be insulated from the adjacent solid electrolyte.

In an example embodiment of the present invention, the third electrode may be arranged in a gas space that may be located in the sensor element, for example, in the coating layer of the reference gas space, and may be connected to a gas region outside the sensor element.

The present invention is illustrated in the drawings and explained in the following description.

DETAILED DESCRIPTION

Figure 1:
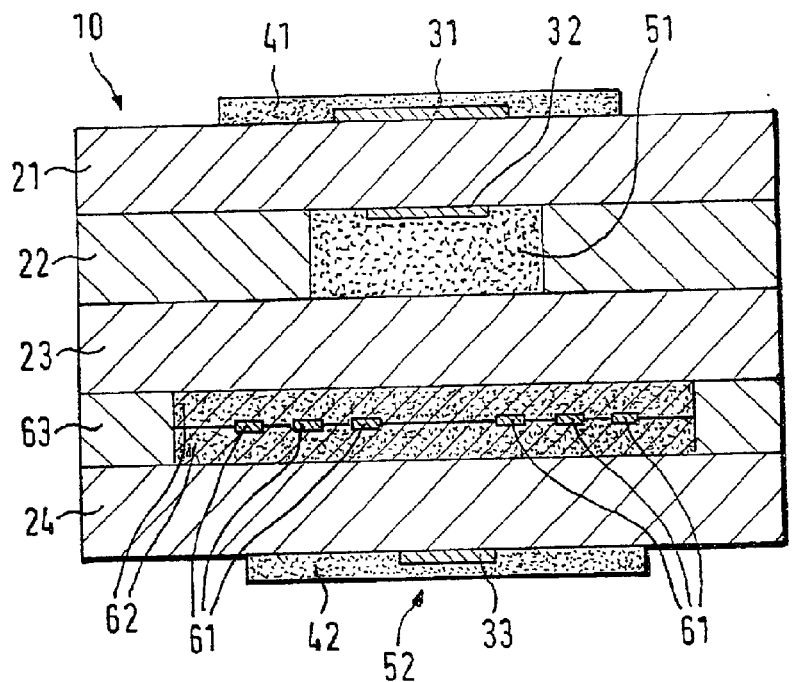
FIG. 1 is a cross-sectional view through a measurement area of a first example embodiment of a sensor element according to the present invention.
Figure 2:
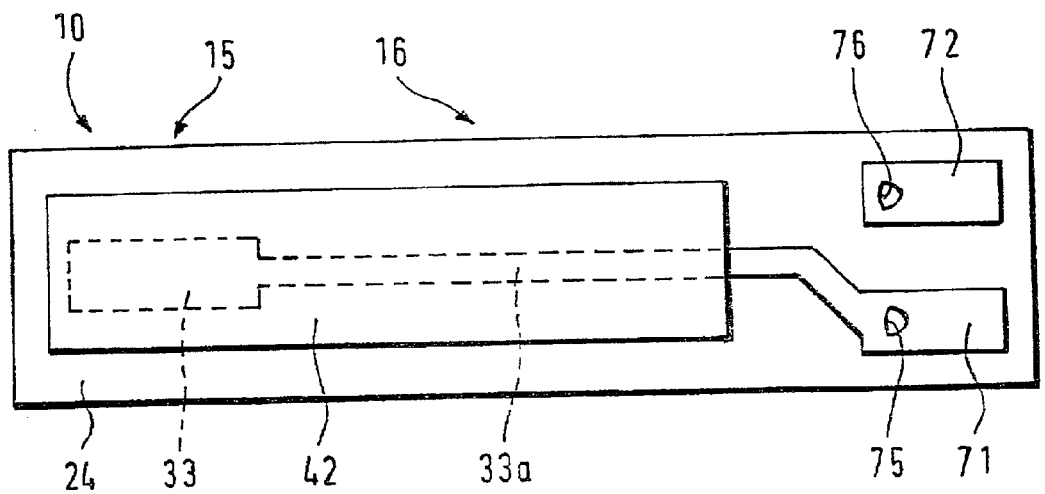
FIG. 2 is a plan view of the example embodiment illustrated in FIG. 1.

The first example embodiment of the present invention, illustrated in FIGS. 1 and 2, has the form of a sensor element 10 of a lambda probe including a measuring area 15 and a supply area 16. Sensor element 10 may be constructed as a layered system and may include first, second, third and fourth layers of solid electrolyte 21, 22, 23, 24. A first electrode 31, coated with protective film 41, may be attached to first electrolyte layer 21 on an external surface of sensor element 10 in measurement area 15. Protective film 41 may be porous, so that first electrode 31 is exposed to a measuring gas. A second electrode 32 may be attached to the side of first solid electrolyte film 21 facing electrode 31. Second electrode 32 may be arranged in a reference gas space provided in second solid electrolyte film 22. Reference gas space 51 may be filled with a porous material.

In order to heat measurement area 15 of sensor element 10, a heater 61 may be provided between third and fourth solid electrolyte layers 23, 24 and may be insulated from the surrounding solid electrolyte films by heater insulation 62. Heater 61 and heater insulation 62 may be enclosed laterally by a sealing body 63, which may be made from an ion-conducting material.

A third electrode 33 may be attached to the external surface of fourth solid electrolyte film 24 and may be coated with additional protective film 42. Additional protective film 42 may be porous, so that third electrode 33 may be in contact with the measuring gas in a gas space 52. Gas space 52 may be the area adjacent to third electrode 33 outside sensor element 10. Third electrode 33 has a smaller surface with respect to the large surface area of sensor element 10 than first and/or second electrodes 31, 32. Third electrode 33 may be electrically connected to a first contact surface 71 by a lead 33a arranged in supply area 16. First contact surface 71 may be arranged on the side of sensor element 10 facing away from measurement area 15 and may serve as the contact for the sensor element. A second contact surface 72 may be provided adjacent to first contact surface 71. First and second contact surfaces 71, 72 may be electrically connected respectively to a first and a second heater lead by a first and a second feedthrough 75, 76, and lead to heater 61. In this manner, third electrode 33 may be electrically connected to first heater lead via lead 33a, contact surface 71 and first feedthrough 75.

A constant potential, for example, a ground potential may be applied to first heater lead and thereby also to third electrode 33 by electronic evaluation arrangement arranged outside the sensor element. A voltage may be applied at heater 61 by a change in the potential at second contact surface 72 to heat measurement area 15 of sensor element 10. The potential of second electrode 32 may be selected so that oxygen may be pumped from third electrode 33 to second electrode 32 and thus also into reference gas space 51 caused by a voltage gradient between second and third electrodes 32, 33. In this manner, it may be assured that the oxygen partial pressure in reference gas space 51 is always adequate.

Figure 3:
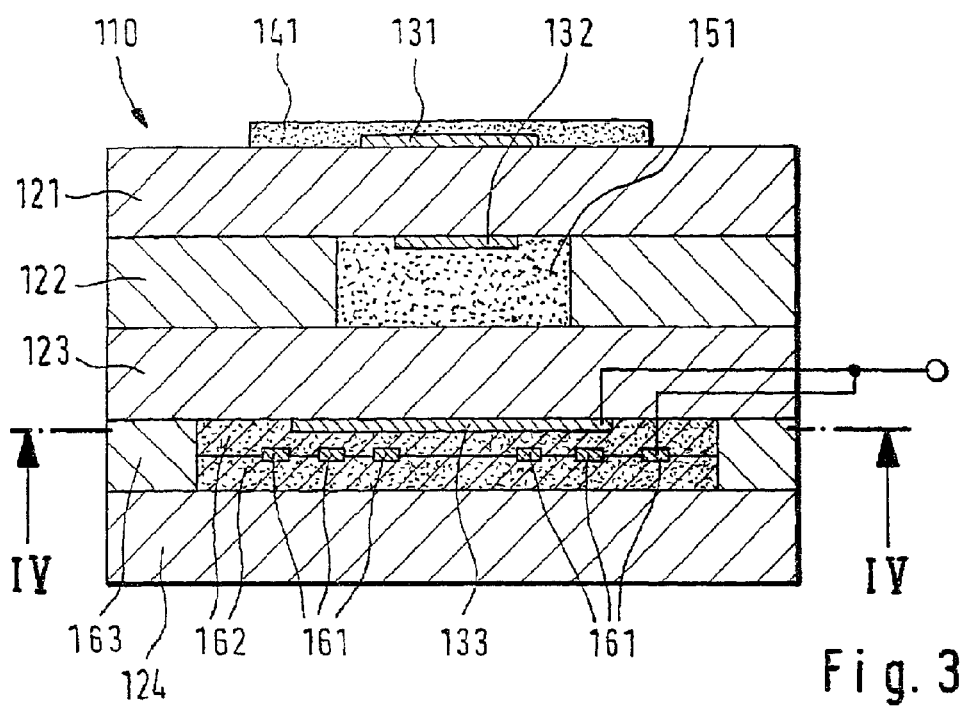
FIG. 3 is a cross-sectional view through a measurement area of a second example embodiment of the sensor element according to the present invention.
Figure 4:
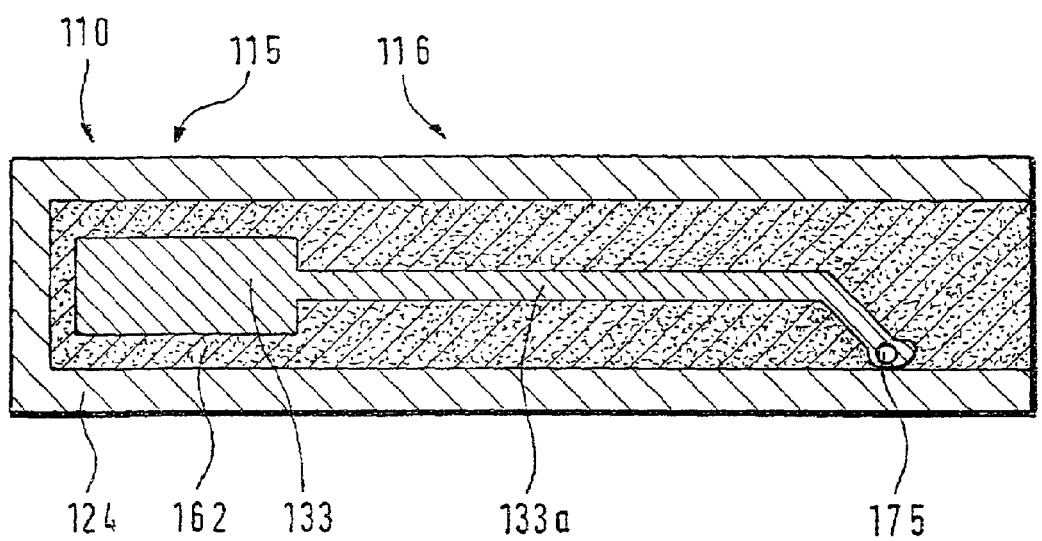
FIG. 4 is a longitudinal cross-sectional view through the measurement area of the second example embodiment corresponding to section line illustrated IV—IV in FIG. 3.

The second example embodiment of the present invention, illustrated in FIG. 3 and FIG. 4, has the form of a sensor element 110 including measurement area 115 and supply area 116. Sensor element 110 may also be constructed as a layered system and may include first, second, third, and fourth solid electrolyte layers 121, 122, 123, 124. A first electrode 131 may be attached to first solid electrolyte film 121, and may be coated with porous protective film 141. A second electrode 132 may be attached to the side of first solid electrolyte film 121 facing first electrode 131. Second electrode 132 may be arranged in a reference gas space 151 provided in second solid electrolyte film 122.

In order to heat measurement area 115 of sensor element 110, as in the first example embodiment, a heater 161 may be provided between third and fourth solid electrolyte layers 123, 124, and may be insulated from the surrounding solid electrolyte layers by heater insulation 162. Heater 161 and heater insulation 162 may be enclosed laterally by a sealing body 163.

The second example embodiment differs from the first example embodiment essentially in that heater insulation 162 is porous, and that a third electrode 133 with lead 133a is provided between heater insulation 162 and third solid electrolyte layer 123. Porous heater insulation 162 is in contact with a gas atmosphere outside sensor element 110, for example, via contact 175 or via a channel on the side of sensor element facing away from measuring area 115. As in the first example embodiment, third electrode 133 is electrically connected to a first heater lead via a feedthrough 175 and is at constant potential. The wiring scheme of electrodes 131, 132, 133 as well as of heater 161 and its leads is the same as for the first example embodiment, and therefore does not require further description.

In a further example embodiment, first heater lead may be arranged at least partly between the heater insulation and the third solid electrolyte layer, and may serve in these areas as a third electrode. Thereby, the possibility of pumping oxygen into the reference gas space via the first heater lead and the second electrode may be assured.

Figure 5:
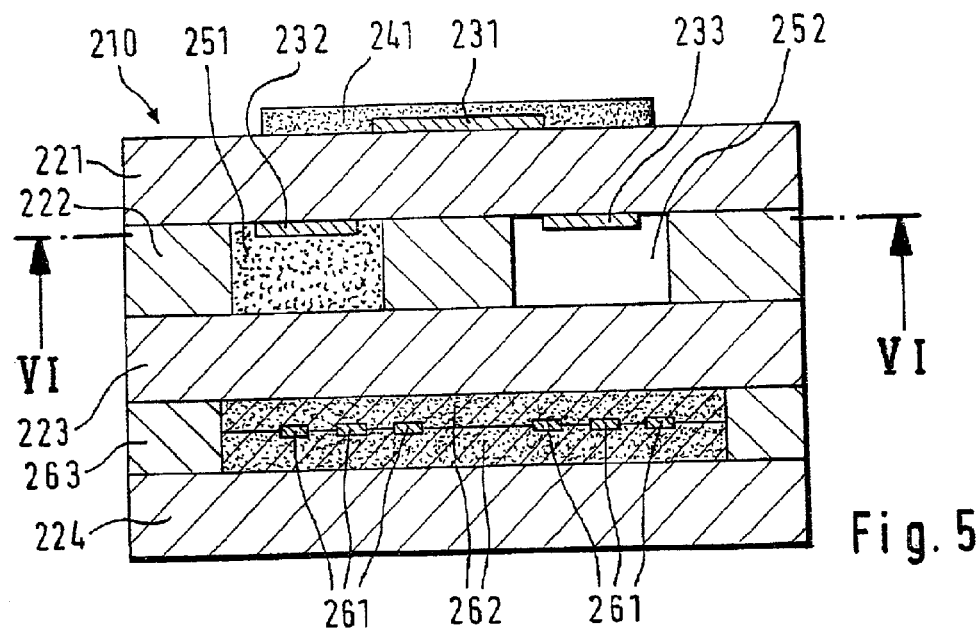
FIG. 5 is a cross-sectional view through the measurement area of a third example embodiment of the sensor element according to the present invention.
Figure 6:
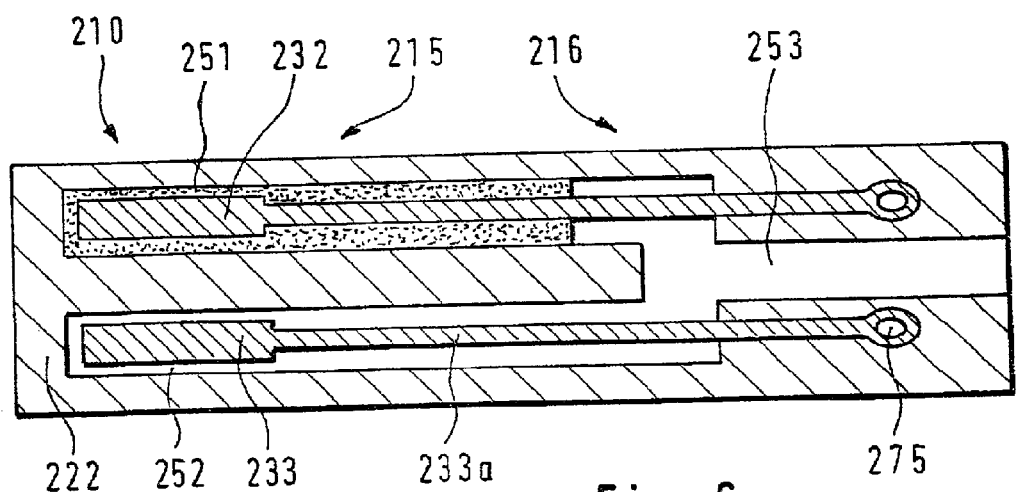
FIG. 6 is a longitudinal cross-sectional view corresponding to a section line VI—VI illustrated in FIG. 5 through the third example embodiment.

A third example embodiment of the present invention, illustrated in FIG. 5 and FIG. 6, has the form of a sensor element 210 including measurement area 215 and supply area 216. Sensor element 210 may include first, second, third, and fourth solid electrolyte layers 221, 222, 223, 224. A first electrode 231 may be attached to first solid electrolyte layer 221, and may be coated with porous protective film 241. A second electrode 232 may be attached to the side of first solid electrolyte film 221 facing first electrode 231. Second electrode 232 may be arranged in a reference gas space 251 provided in second solid electrolyte film 222.

In order to heat measurement area 215 of sensor element 210, as in the first and second example embodiments, a heater 261 may be provided between third and fourth solid electrolyte layers 223, 224, and may be electrically insulated from the surrounding solid electrolyte layers by heater insulation 262. Heater 261 and heater insulation 262 may be enclosed laterally by a sealing body 263.

The third example embodiment differs from the first and second example embodiments essentially in that a third electrode 233 with lead 233a is provided in an additional gas space 252, which is included in second solid electrolyte film 222 in addition to reference gas space 251 that is filled with a porous material. Reference gas space 251 and additional gas space 252 are combined in a common gas channel 253 in supply area 216 of sensor element 210. This channel is in contact with a reference gas atmosphere outside sensor element 210 on the side of sensor element 210 facing away from measuring area 215. Reference gas space 251 and additional gas space 252 are configured so that (even without pumping into the reference gas space) the diffusion current of the gas outside sensor element 210 to third electrode 233 is greater than that to second electrode 232. This may be assured, for example, by filling reference gas space 251 with a porous material, while additional gas space 252 is configured as a cavity, or if the porous material in reference gas space 251 has a smaller percentage of porosity than a porous material provided in additional gas space 252.

As in the first example embodiment, third electrode 233 is electrically connected to a first heater lead via a feedthrough 275 and is at constant potential. The wiring scheme of electrodes 231, 232, 233 as well as heater 261 and its leads is the same as for the first example embodiment, and therefore does not require further description.

In a further improvement of the third example embodiment, the additional gas space may be arranged in a solid electrolyte layer other than second solid electrolyte layer 222. The additional gas space may also be in contact with a gas space arranged outside the sensor element via a channel that is not connected with the reference gas space.

In another example embodiment, a fourth electrode may be provided in the reference gas space on the third solid electrolyte film, and may be electrically connected to the second electrode. This enables the reference gas space also to be filled by pumping via the fourth electrode.

In the example embodiments, reference gas space 51, 151, 251 may be in contact with a reference gas located outside sensor element 10, 110, 210 via an aperture in the side of sensor element 10, 110, 210 facing away from measurement area 15, 115, 215. Reference gas space 51, 151, 251 may be in contact with the measuring gas via an appropriately selected aperture.

The pumping current into reference gas space 51, 151, 251 may be selected such that it is greater than the diffusion current into reference gas channel 51, 151, 251 in the area of second electrode 32, 132, 232. A stable reference was achieved with a pumping current greater by a factor of 4 than the diffusion current. The porous material that fills reference gas space 51, 151, 251 was selected for the example embodiments described such that with a typical partial pressure differential between reference gas space 51, 151, 251 and the gas atmosphere present prevailing outside sensor element 10, 110, 210, the diffusion current is 5 $\mu$A. It proved sufficient to set the pumping current to a value from 5 to 50 $\mu$A by appropriate selection of the voltage differential between second electrode 32, 132, 232 and third electrode 33, 133, 233.

The gas sensor described may be suited for installation on the gas outlet side of a catalytic converter.

What is claimed is:

1. A gas sensor for determining a physical quantity of a gas component, comprising:
   a sensor element including at least one electrochemical cell including:
   a first electrode;
   a second electrode, the first electrode and the second electrode set apart on at least one solid electrolyte, the second electrode arranged in a reference gas space; and
   a third electrode in contact with a gas located in a gas space, and the gas component exchangeable between the gas space and the reference gas space by a voltage applied between the second electrode and the third electrode, the gas space being arranged in a same layer plane as the reference gas space, and the gas space and the reference gas space being connected to a reference-air atmosphere outside the sensor element via a common gas channel.

2. The gas sensor according to claim 1, wherein the reference gas space is at least partly filled with a porous material.

3. The gas sensor according to claim 2, wherein the sensor element includes a heater arranged in a measuring area, the heater supplied by a first and a second heater lead in a supply area of the sensor element, the heater electrically insulated from the surrounding solid electrolytes by heater insulation.

4. The gas sensor according to claim 3, wherein the second heater lead is electrically insulated from surrounding solid electrolytes by the heater insulation.

5. The gas sensor according to claim 3, wherein the first and the second heater leads are electrically insulated from surrounding solid electrolytes by the heater insulation.

6. The gas sensor according to claim 1, wherein the gas space is arranged inside the sensor element.

7. The gas sensor according to claim 1, wherein the third electrode has a smaller surface in a layer plane of the sensor element than at least one of the first electrode and the second electrode.

8. The gas sensor according to claim 1, wherein the electrochemical cell is configured to be potentiometrically driven.

9. The gas sensor according to claim 1, wherein the sensor element includes an amperometrically driven electrochemical cell including a first pump electrode in a measuring gas space and a second pump electrode on an exterior surface of the sensor element, an exhaust gas configured to penetrate the measuring gas space through a diffusion barrier.

10. The gas sensor according to claim 1, further comprising a fourth electrode arranged in the reference gas space, the fourth electrode electrically connected to the second electrode, a gas component exchangeable between the reference gas space and the gas space via the fourth and the third electrode.

11. The gas sensor according to claim 1, wherein the second and third electrodes are configured to receive an alternating voltage between them, a temperature of the measuring area of the sensor element calculable in accordance with an impedance.

12. The gas sensor according to claim 11, wherein a gas component is configured to be pumped into the reference gas space from the gas space by an application of a voltage, a pumping current having a value of 5 to 50 $\mu$A.

13. The gas sensor according to claim 12, wherein the pumping current is approximately 20 $\mu$A.

14. The gas sensor according to claim 1, wherein, via an aperture, the reference gas space is in contact with gas located outside the sensor element on a side of the sensor element facing away from a measuring area.

15. The gas sensor according to claim 14, wherein the reference gas space is in contact with at least one of a measuring gas and the reference gas.

16. The gas sensor according to claim 1, wherein the gas sensor is configured to determine the physical quantity of an exhaust gas of an internal combustion engine.

17. A gas sensor for determining a physical quantity of a gas component, comprising:
   a sensor element including at least one electrochemical cell including:
   a first electrode;
   a second electrode, the first electrode and the second electrode set apart on at least one solid electrolyte, the second electrode arranged in a reference gas space, the reference gas space being at least partly filled with a porous material;

a third electrode in contact with a gas located in a gas space, and the gas component exchangeable between the gas space and the reference gas space by a voltage applied between the second electrode and the third electrode; and a heater arranged in a measuring area, the heater supplied by a first and a second heater lead in a supply area of the sensor element, the heater electrically insulated from the surrounding solid electrolytes by heater insulation, the heater insulation including a porous configuration and forming the gas space, the porous heater insulation connected to gas located outside the sensor element;

wherein at least portions of the first heater lead are arranged between a solid electrolyte and the porous heater insulation, and the first heater lead is configured as the third electrode.

* * * * *